United States Patent [19]

Snyder et al.

[11] Patent Number: 5,110,566
[45] Date of Patent: May 5, 1992

[54] CHROMATOGRAPHIC SEPARATION OF ZIRCONIUM ISOTOPES WITH REDUCED WASTE LIQUOR

[75] Inventors: Thomas S. Snyder, Oakmont, Pa.; Ernest D. Lee, Ogden, Utah

[73] Assignee: Westinghouse Electric Corp., Pittsburgh, Pa.

[21] Appl. No.: 555,342

[22] Filed: Jul. 19, 1990

[51] Int. Cl.$^5$ .............................................. C22B 34/10
[52] U.S. Cl. .......................................... 423/70; 423/2; 423/21.5; 423/76; 423/73; 423/DIG. 7; 75/612; 210/656; 210/660
[58] Field of Search ............... 423/70, 73, 76, 2, 21.5, 423/DIG. 7; 75/612; 210/656, 660; 502/401

[56] References Cited

U.S. PATENT DOCUMENTS

| | | | |
|---|---|---|---|
| 2,546,953 | 3/1951 | Street, Jr. | 210/656 |
| 2,759,793 | 8/1956 | Lister et al. | 423/70 |
| 3,971,842 | 7/1976 | Ewbank | 210/660 |
| 4,584,183 | 4/1986 | Chiang et al. | 423/70 |

OTHER PUBLICATIONS

Byers et al., "Pilot Scale Studies of Sugar Separations by Continuous Chromatography".

Primary Examiner—Theodore Morris
Assistant Examiner—Edward Squillomte

[57] ABSTRACT

The isotopes of zirconium can be partially or completely separated by loading an aqueous solution of an ionic compound of zirconium onto a cationic exchange resin with pentavalent phosphorus derived active groups which serves as the stationary phase of a chromatograph, eluting the compound with an aqueous acid and collecting distinct elution volumes representative of each isotope. In a preferred embodiment, the eluant is a strong mineral acid, such as hydrochloric acid and the chromatograph is of a type, such as a continuous annular chromatograph, that it can be operated in a continuous, steady state manner.

15 Claims, 5 Drawing Sheets

CHROMATOGRAPHIC SEPARATION OF ZIRCONIUM ISOTOPES WITH REDUCED WASTE LIQUOR

FIELD OF THE INVENTION

The present invention is concerned with processing zirconium to obtain a lower average thermal neutron capture cross section by a partial or complete separation of its isotopes thus improving its suitability as an internal material of construction for a nuclear reactor, for instance, as a fuel rod cladding.

BACKGROUND OF THE INVENTION

Zirconium metal has historically been a material of construction, in particular cladding for fuel rods, for nuclear reactors, and there has been a continuing interest in reducing its tendency to adsorb thermal neutrons. The more transparent the internal materials of construction of a nuclear reactor are to such thermal neutrons the more efficiently the reactor will function since a certain number of these neutrons are necessary to sustain the nuclear reaction and their production must compensate for the adsorption by the internal materials of construction. Early efforts were directed to separating zirconium from hafnium. The two elements occur together naturally but the hafnium has a substantially larger capture section for thermal neutrons. Such efforts involved both chromatographic techniques using an ion exchange resin and various solvent extraction techniques.

Recent efforts have been directed to isolating a zirconium isotope with either a particularly high or a particularly low cross section to thermal neutrons. This allows the production of a zirconium with a lower average cross section than one composed of the naturally occurring isotope distribution. These efforts at isotope separation have generally involved some type of solvent extraction. These separation techniques are generally only able to separate one isotope at a time. Thus they do not provide a means for simultaneously isolating the zirconium 90 and 94 isotopes which are recognized as having particularly small cross sections (one source lists them as 0.055 and 0.031 Barns, respectively, as compared to 0.567 Barns for zirconium 91 and 0.1430 for zirconium 92).

More recently, it has been proposed that isotopes of zirconium could be separated in an economically practical manner by the use of continuous steady state chromatography utilizing a cation exchange resin as the stationary phase. The preferred stationary phase in this proposal was sulfonated crosslinked polystyrene beads. It appears that this proposal provides a continuous process for isolating both of the abundant low thermal cross section isotopes, zirconium 90 and zirconium 91, in a single procedure. However, it is difficult to get the concentration of zirconium in the product of elution volumes as high as desired. Thus, larger than desired volumes of spent eluant must be dealt with and this poses a problem of waste management. This concentration can be increased by shortening the residence time on the chromatograph and this in turn can be achieved by increasing the separation capacity of a theoretical stage without adversely effecting the achievable flow rates through the column. Such an improvement in theoretical stage efficiency would also permit the same separations to be effected on shorter columns.

It is an object of the present invention to provide an improved process for chromatographically separating the isotopes of zirconium which conveniently yields improved concentrations of zirconium in the product elution volumes, and reduces the volume of waste liquor to be recycled or processed for disposal.

It is a further object of the present invention to provide a process which allows the use of shorter chromatographic columns thus reducing both the capital and operating costs of the process. It is an additional object of the present invention to provide a process which yields separate waste streams of heavy metal waste and radio chemical waste each with an increased solids content. Another object of the present invention is to provide a process which utilizes a cation exchange resin which yields a higher theoretical stage separation without impairing the flow rates achievable on the column.

SUMMARY OF THE INVENTION

A process for the partial or complete separation of the isotopes of zirconium using chromatography has been developed in which a cation exchange resin with active groups derived from pentavalent phosphorus is the stationary phase, an aqueous solution of an ionic compound of a mixture of zirconium isotopes is the feed, and an aqueous acid solution is the mobile phase. The process involves the mobile phase eluting the zirconium isotopic solute, under conditions such that each of the various naturally occurring isotopes of zirconium is primarily eluted in an elution volume distinct from the elution volumes of the other isotopes. In a preferred embodiment the conditions are such that at least one of the elution volumes contains essentially only one isotope of zirconium. The process is preferably conducted in a steady state, continuous manner, and it is particularly preferred to conduct it in a continuous annular chromatograph.

A particular preferred embodiment involves feeding zirconium chloride dissolved in water to a continuous annular chromatograph with a stationary phase which comprises a cation exchange resin with active groups derived from one of the groups consisting of tributyl phosphate, tri-n-octyl phosphine oxide, di-2-ethylhexyl phosphoric acid and mixtures thereof. The mobile phase for the elution is preferably aqueous hydrochloric acid.

DETAILED DESCRIPTION OF THE INVENTION

The stationary phase can be any cation exchange resin with active groups derived from pentavalent phosphorus which have an affinity for zirconium cations—typically in aqueous solution as $ZrO^{+2}$ but which may also be complexed with $Cl^-$, $SO_4^-$, $VO_3^-$ or $PO_4^{-3}$ depending on the acid solvent. It is preferred that the cation exchange resin be capable of displaying a very strong affinity for such cations as reflected by a large solid to liquid distribution coefficient (defined as Kd=C resin/C liquor) in dilute mineral acid solutions. It is particularly preferred that this coefficient be in excess of about 100 in acid solutions of less than about 0.3 Normal. It is particularly preferred to utilize cation exchange resins with the highest capacities possible—typically between about 0.01 and 0.5 milliequivalents per milliliter with a most probable capacity of about 0.1 milliequivalents per milliliter under elution conditions.

It is also preferred that the stationary phase comprise a monodisperse distribution of spherical particles with an average particle size of less than about 10 microns, more preferably less than about 1 micron. An especially preferred stationary phase comprises resin beads carrying active groups derived from tri-n-octyl phosphine oxide, tributyl phosphate or di-2-ethylhexyl phosphoric acid, especially the last of these.

The feed phase may be any convenient solution of ionic zirconium compounds formed from a mixture of zirconium isotopes. The isotope mixture may be that which occurs in nature or it may be a partially refined mixture obtained from a preliminary refinement process.

A preferred feed phase is that obtained from dissolving zirconium tetrachloride. Crude zirconium is commercially obtained by chlorinating zircon sand in the presence of coke at about 1000° C. and separating the resulting zirconium tetrachloride from the resulting silicon tetrachloride by means of a differential condenser. The zirconium fraction typically contains a natural distribution of isotopes and also contains hafnium tetrachloride. Both compounds are readily hydrolyzed to yield an aqueous solution suitable for use in a chromatographic process. It is preferred to adjust the pH of this solution to the acid side, particularly to between about 3 and 4 to reduce the chemical shock to the stationary phase in elution with a highly acidic eluant.

It is preferred that the feed phase be as concentrated a possible without exceeding the solubility limit for the solute. In the preferred feed phases, the solubility limit is about 90 g/l.

The mobile phase may be an aqueous acid solution capable of solvating the zirconium ions such that they can be eluted down the column. This mobile phase or eluant is a fluid capable of displacing the zirconium ions from their ionic association with the stationary phase. It is preferably an aqueous solution of a strong mineral acid such as hydrochloric acid or nitric acid. Particularly preferred are sulfuric acid and hydrochloric acid, with hydrochloric acid being especially preferred. The acid strength needed is dependent on the identity of particular acid utilized but acid strengths of about one Normal or greater are preferred. If the mobile phase contains hafnium ions, it is preferred to use an acid solution in which the zirconium has a greater affinity for the stationary phase than the hafnium as reflected in the solid to liquid distribution coefficients. An especially preferred eluant is between about 1 and 6 more preferably between about 3 and 6 Normal aqueous hydrochloric acid, particularly when the mobile phase contains hafnium ions.

The preference for a hydrochloric acid eluant is based on both its advantageous chemical and transport interactions with hafnium and zirconium and its compatibility with readily available feedstock. The separation of hafnium from zirconium and the separation of the zirconium isotopes is particularly efficient with this class of eluants, indicating that it promotes an optimum balance of affinity to and release from the resin bends. The commercially available feedstock is obtained by chlorinating zircon sand and the resultant hafnium and zirconium tetrachlorides are, of course, highly compatible with hydrochloric acid.

The effective column height should be sufficient to allow significant resolution of the various isotopes of zirconium into distinct product fractions. The resolution is preferably sufficient to yield an isotope purity in excess of about 90 percent, more preferably at least about 98 percent. It is preferred that this resolution be effected in a single pass through the column. The effective column height needed for a given resolution can be estimated from an application of the Kremser-Brown-Saunders equation, to empirical data on the separation capacity of a given stationary phase, mobile phase, eluant and flow conditions.

An inherent result of a resolution of the isotopes of a zirconium is an efficient separation of hafnium from zirconium. A process sufficiently sensitive to separate isotopes of zirconium will readily effect a separation of zirconium from hafnium as well.

A separation factor, $\alpha$, is used to define the ability to separate the zirconium isotopes. This factor is itself defined by the following formula for the binary case:

$$\alpha = \frac{y/(1-y)}{x/(1-x)} \quad (1)$$

wherein y is the molar concentrations of the desired isotope in the product faction rich in that isotope and x is the molar concentration of this same isotope in the tails fraction. Approximate calculations can be performed by selecting one isotopic fraction as the product, and defining the tails fraction as the composite of the other product fractions. Thus, if a product fraction is obtained in which 98% of the zirconium is zirconium 90 and if in the composite of all the other product fractions together only 2% of the zirconium is zirconium 90, the $\alpha$ defining this separation would be $$\frac{0.98/(1-0.98)}{0.02/(1-0.02)} = 2401$$

Separation factors, $\alpha$, for isotopic separations are conveniently evaluated on 25 to 100 cm columns with the 25 cm length being preferred. For such columns $\alpha$ values for zirconium 90 on the preferred stationary phases with the preferred eluants are greater than about 1.05, preferably greater than about 1.085.

The strong affinity of cation exchange groups derived from pentavalent phosphorus for zirconium cations facilitates the achievement of large separation factors, $\alpha$, for isotopic separation. This focus has been overlooked in traditional thinking which screened potential isotopic separation media on the basis of their respective efficiencies in separating hafnium from zirconium. In fact, a high efficiency in separating hafnium from zirconium is not necessarily linked to a high efficiency in separating the isotopes of zirconium.

Generally, the separation factor of a theoretical stage can be improved by either increasing the surface area of the beads of exchange resin or by changing the chemical nature of the cation exchange groups. The former approach usually entails a decrease in achievable flow rates through the column as a result of decreased permeability of the stationary phase. The latter approach provides a means for enhancing the separation capability.

The present invention proposes that selecting the pentavalent phosphorus derived of cation exchange groups which have a high affinity for zirconium cations will facilitate such an increase in the separation factor for isotopic separation. Thus, columns can be more readily constructed and operated which yield a desirable balance of separation capacity and flow rate.

The effective column length required for any desired degree of purification is then determined from this data. For instance, if a 25 cm test column yields a separation factor, $\alpha$, of 1.085 this can be used as the separation factor for a theoretical stage, $\alpha_s$, in applying the Kremser-Brown-Saunders equation in estimating the number of theoretical stages, N, required. This formula can be used in the form:

$$N = \frac{\ln \alpha_r}{\ln \alpha_s}$$

For the case being discussed this yields the following result:

$$N = \frac{\ln 2401}{\ln 1.085} = 95.4$$

Thus, 95.4 theoretical stages of 25 cm each are required which implies an effective column length of about 24M.

The following table shows projected column length as a function of $\alpha$ and desired product purity. It is based on the assumption that the Kremser-Brown Saunders equation holds in the Underwood-Fenske form assuming the binary mixture approximation:

| | 98% Purity | | 98% Purity | |
|---|---|---|---|---|
| $\alpha$ for 0.25 M Test Column | Number of Stages | Total Column Length (M) | Number of Stages | Total Column Length (M) |
| 1.001 | 7830 | 1960 | 4970 | 1744 |
| 1.01 | 786 | 200 | 500 | 175 |
| 1.03 | 265 | 66 | 168 | 42 |
| 1.09 | 102 | 26 | 65 | 16 |
| 1.1 | 82 | 21 | 52 | 13 |

Thus, an increase in the separation factor for a theoretical stage, $\alpha_s$, allows a decrease in the total column length needed to effect a given degree of separation. This, of course, reduces the capital costs involved in conducting the process. If this increase is effected without a concomitant loss in permeability, it can also facilitate running the process at a lower pressure further reducing capital costs and also reducing maintenance costs. A shorter column with equivalent permeability will require a lower pressure to maintain the same flow rate. Of course, lower pressure operations normally involve less expensive equipment and entail lower maintenance expense.

The effective column height can be vertical but it may have other orientations. What is important is the effective path over which the mobile phase travels.

It is preferred that the path be provided in such a way that the chromatographic separation can be operated continuously. There is no convenient technique currently available for instantaneously sensing the concentration of any given isotope of zirconium. Thus, there is a preference for a continuously operating procedure which has reached steady state so that a particular product fraction reproducibly has a certain isotope distribution. If the chromatographic separation is effected in a discontinuous or batch manner random variations between runs may make it difficult to reproducibly collect product fractions with the same isotope distributions from run to run. For instance, if a single vertical column is loaded in a batch manner the elution time of the product fraction rich in a particular isotope may vary from run to run due to random variables difficult to control such as feed concentration fluctuations, etc.

A particularly preferred continuously operating chromatograph is the continuous annular chromatograph. This device was developed by Oak Ridge National Laboratory and comprises an annular stationary phase which is rotated about the axis of the annulus. The annulus is provided by packing the stationary phase material, such as resin beads, between two concentric cylinders of differing diameters with vertical axes. A feed port is provided at a given angular position and one or more eluant ports are provided at some angular offset from the feed port. It is preferred to place a layer of glass beads above the stationary phase, and to feed the eluant onto the top of the glass bead layer while feeding the zirconium feedstock directly to the top of the stationary phase by having its feed nozzle or nozzles extend through the glass bend layer. This should prevent any undesired mixing effects.

This device is provided with a number of product ports set at a number of angular positions which can be set arbitrarily to accommodate a particular set of operating condition. Each product port collects an elution volume which has had a particular residence time on the column. The stationary phase is typically rotated at a constant speed so that any vertical segment of the annular bed is above a particular fixed product collection port at a given time after this segment has been loaded with zirconium feedstock and eluant. Thus, each product collection port has an angular position which corresponds to a particular elution time for a particular rate of rotation of the stationary phase and for a particular flow rate through the stationary phase.

The flow rate through the stationary phase is controlled by the pressure drop across the effective height of the stationary phase and the physical characteristics of the stationary phase, i.e., particle size and packing void volume. This pressure drop may be provided by the hydrostatic head of the feedstock and eluant but it is preferably provided by pressurizing the device. The pressure required to achieve a particular flow rate is governed by the nature of the stationary phase (i.e. its packing, average particle size and particle size distribution); the smaller the average particle of the resin beads making up the stationary phase the larger the pressure drop required to obtain a particular flow rate over a particular effective height. However, the separation factor for any given theoretical stage is improved as the average particle size of the resin beads is decreased. Thus, the effective height needed to effect a given degree of separation is decreased as the separation capacity of a unit length (or theoretical stage height) is increased by decreasing the average particle size of the resin beads.

The use of pentavalent phosphorus derived cation exchange groups enables a favorable combination of flow rate and effective column height which minimizes the residence time on the column. These groups allow desirable isotopic separations to be effected on short columns with good permeability.

A short residence time on the column allows an increase in the zirconium concentration in the product elution volumes. In general, the longer the residence time on the column, the more "band spreading" which occurs. "Band spreading" is a term of art used in this context to indicate the phenomenum that the longer a particular product fraction is resident on a column, the larger proportion of the total elution volume which contains some of the desired product. Thus to obtain all or a certain percentage of this product fraction it is necessary to collect a volume of eluant which increases with residence time. Thus, the net effect of band spreading is to dilute the metal concentration in the product fractions.

The flow rate across the effective height of the stationary phase and the rotational speed of the stationary phase should be coordinated such that a particular product fraction always elutes at the same angular position and thus is always delivered to the same product collection port.

It is preferred that the chromatograph be operated in a displacement mode wherein no more than about 5 percent, more preferably no more than about 1 percent of the effective column height, is loaded with feed solution before elution is initiated. This is conveniently effected by using a feed solution which has insufficient acid strength to release the zirconium cations from ionic bonding with the cation exchange resin and loading no more than about 5 percent, preferably about 1 percent of the effective height, before adding an eluant of sufficient strength to cause the zirconium cations to migrate down the column at a reasonable rate. In the continuous annular chromatograph this end is achieved by coordinating the angular displacement between the feed port and the eluant port and the speed of rotation of the annular bed so that the time interval between loading and elution is just sufficient for the desired degree of penetration. The relationship between the time for loading and the depth of penetration is in turn governed by the flow rate through the annular bed.

The displacement may be effected by either an isocratic or a gradient supply of eluant. In the former case, the eluant can simply be supplied from a single port while in the latter case, several ports at successively greater angular displacements from the feed port are utilized. In the gradient mode, elution under the influence of the initial eluant is permitted to proceed until some separation of the zirconium isotopes has been effected and then eluant with a higher hydrogen chloride concentration is supplied. This increases the migration speed of the zirconium cations down the column and minimizes the range of elution volumes or times over which a given component or product fraction will exit the column or, in other words, this procedure minimizes the band spreading.

Decreasing the elution volumes by gradient elution or by other means increases the concentration of the product, i.e., the zirconium isotope, in the product fraction. Concentrations greater than about 5 g/l, especially between about 20 and 70 g/l are preferred. It is preferred to maximize the concentration of product thereby reducing the total volume of fluid to be processed. This allows a reduction in the overall size of the system with a consequent reduction in capital and operating expenses. However, practical considerations such as solubility limits constrain the maximum concentrations obtainable.

The flow rate down the column is governed by the pressure drop from the top to the bottom of the column and the nature of the stationary phase. The smaller the average particle size of the resin beads making up the stationary phase the higher the pressure drop required to obtain a given flow rate. This relationship is also effected by the particle size distribution of these resin beads. There is, however, a maximum attainable flow rate for any given cation exchange resin stationary phase which cannot be exceeded by the application of additional pressure. The suppliers of such resins rate them in terms of flow rate per given pressure drop and maximum attainable flow rate.

It is preferred to use a stationary phase which will permit flow rates between about 2 and 80, more preferably between about 3 and 20 gallons per minute per square foot of cross sectional area (between about $1.36 \times 10^{-3}$ and $5.43 \times 10^{-2}$ m$^3$/sec, more preferably between about $2.04 \times 10^{-3}$ and $1.36 \times 10^{-2}$ m$^3$/sec per square meter of cross sectional area). There is a relationship between the achievable flow rates and the effective column height needed for a given degree of purity. For a given system of stationary phase and eluant, the theoretical stage separation factor, $\alpha_s$, of the stationary phase will increase as the average particle size of the resin beads of the stationary phase decrease. However, as this particle size decreases so does the flow capacity of the stationary phase. Thus, there is an inverse relationship between $\alpha_s$ and the flow capacity. Thus, a higher flow rate will require a greater effective column height to achieve the same degree of separation or product fraction purity.

Furthermore, there is the additional constraint that the pressure required to achieve the desired flow rate not exceed the capability of available pumps, seals and feed tubing. The required pressure is a function of both the pressure drop needed per unit of effective height and the total effective height required for the desired degree of separation. Thus, as the flow capacity of the stationary phase is increased by a change in its physical configuration and consequently its theoretical stage separation factor, $\alpha_s$, is decreased, the required effective height and the required overall pressure drop are both increased. On the other hand, as the theoretical stage separation factor, $\alpha_s$, is increased by a change in the resin bead size distribution and consequently the flow capacity of the stationary phase is decreased, the pressure drop for a given effective height is increased. A pressure drop of less than about 2758 kPa (400 psi) more especially between about 345 and 1042 kPa (50 and 150 psi) is preferred.

Thus, to obtain a system with a commercially practical capacity, it is necessary to use a stationary phase which will simultaneously display both a reasonable theoretical stage factor, $\alpha_s$, and a reasonable flow rate per unit of effective height with a reasonable pressure drop. This can be achieved by an appropriate selection of both the ionic capacity of the stationary phase cation exchange resin and the eluant.

In a preferred mode several product collection ports are used to collect a particular product fraction. This is accomplished by closely spacing these collection ports so that they more than span the angular range of rotation that corresponds to the elution time interval of that particular fraction but do not extend to angular positions at which any significant portion of any other product fraction is expected to elute. Of course, this requires that the elution time intervals or different product fractions do not substantially overlap. This arrangement tends to insure that minor fluctuations in the steady state elution behaviour which would cause a slight advancement or retardation of the elution time of the desired product fraction will not result in any loss of this fraction.

A particular preferred device for use in practicing the present invention is illustrated in FIGS. 1 through 5. The continuous annular chromatograph 10 illustrated in FIG. 1 comprises two concentric cylinders 30 and 35 which define the annular space 32 seen in FIG. 2. Atop this annular space 32 is a distributor plate 20. Feed pipes or channels 21 and 23 run through the distributor plate 20 and terminate in feed nozzles 22 and 24, respectively. The feed nozzles 22 are intended to supply the feed phase to the exchange resin beads 27 which are packed in the annular space 32. For ease of illustration, these beads are shown as only partially filling the annular space 32. On the other hand, the feed nozzles 24 are intended to feed the eluant to the layer of glass beads 26 which sits atop the exchange resin beads 27. Thus the feed nozzles 24 are somewhat shorter than the feed nozzles 22. This feed arrangement serves to avoid any back mixing of the feed phase.

The central cavity defined by the inner cylinder 35 is sealed by a cap 31 so that pipe or channel 25 can be used to apply pressure to the annular bed of resin beads 22.

Figure 1:
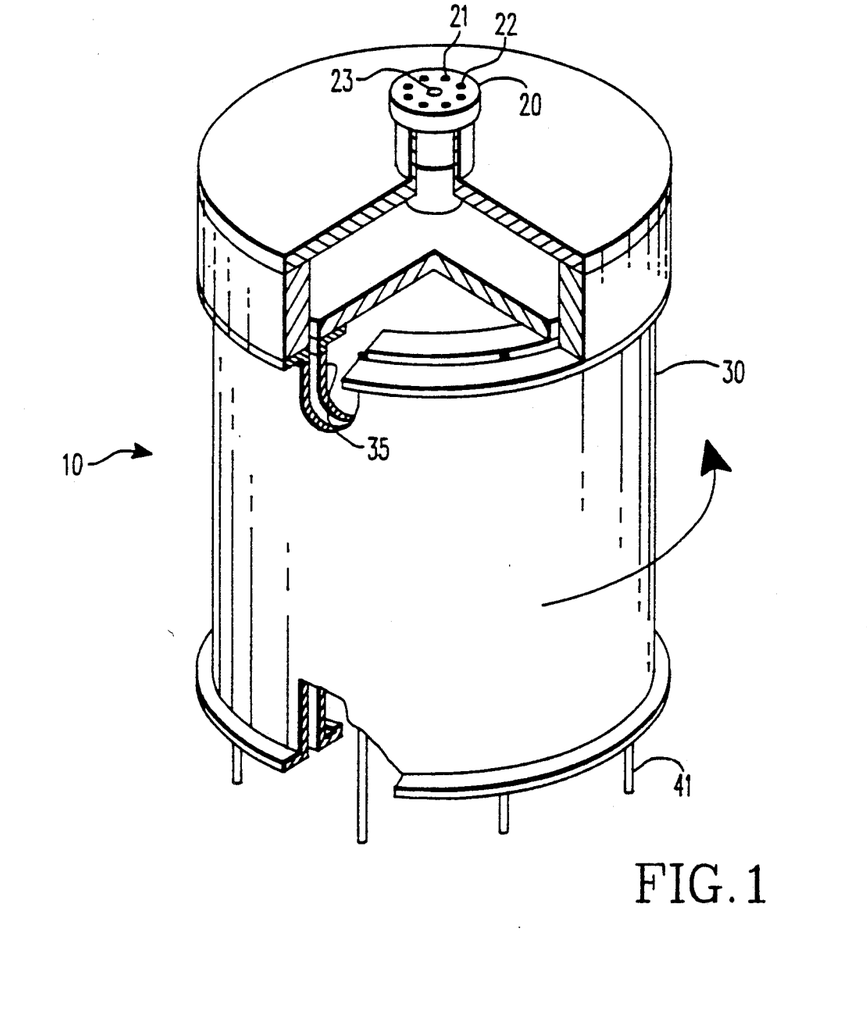
FIG. 1 is a perspective view of a continuous annular chromatograph (CAC) with a portion in section to illustrate the annular construction.
Figure 2:
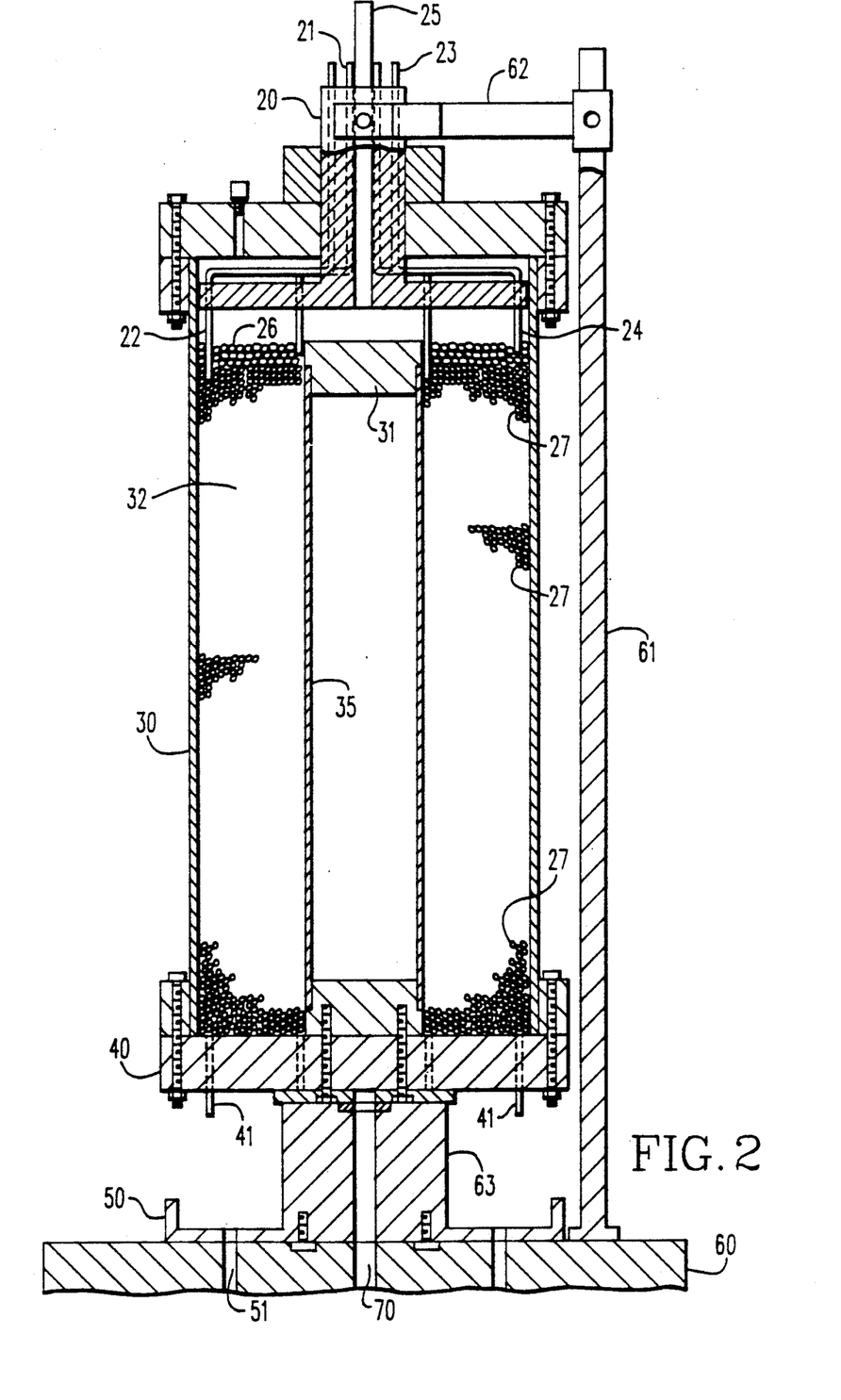
FIG. 2 is a horizontal sectional view of the CAC along a diameter of the concentric circles defining the annulus.
Figure 3:
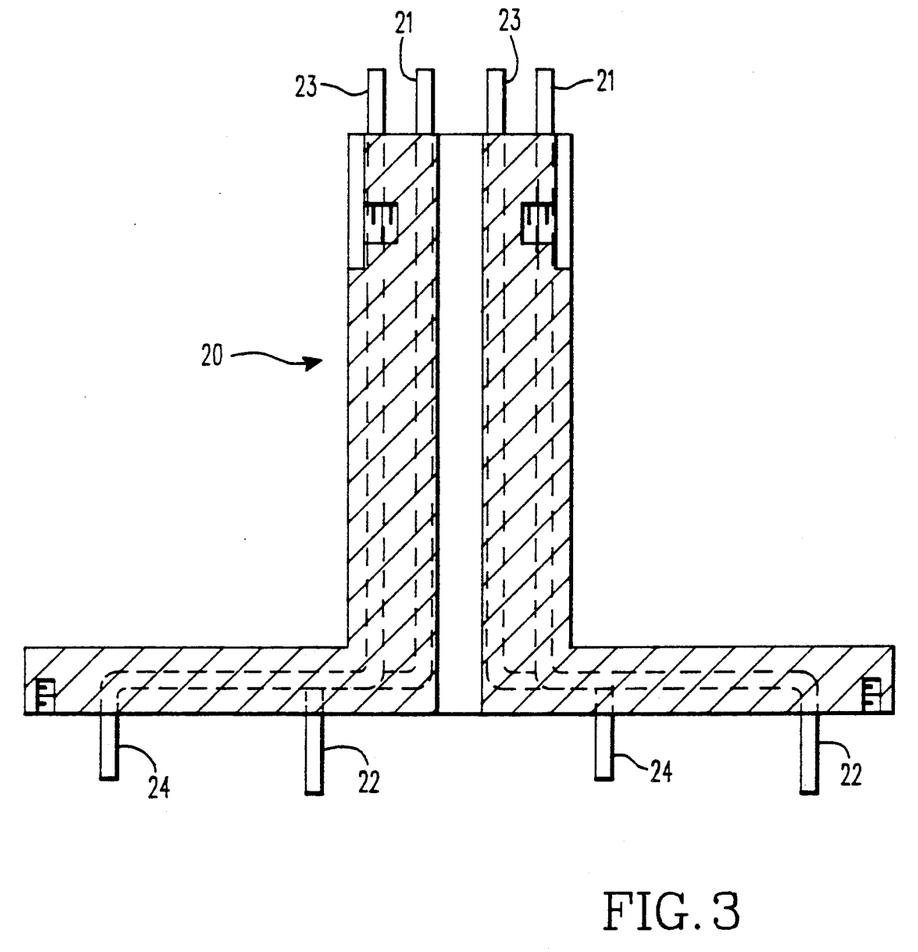
FIG. 3 is an enlarged horizontal sectional view of a part of the top portion of the CAC.
Figure 4:
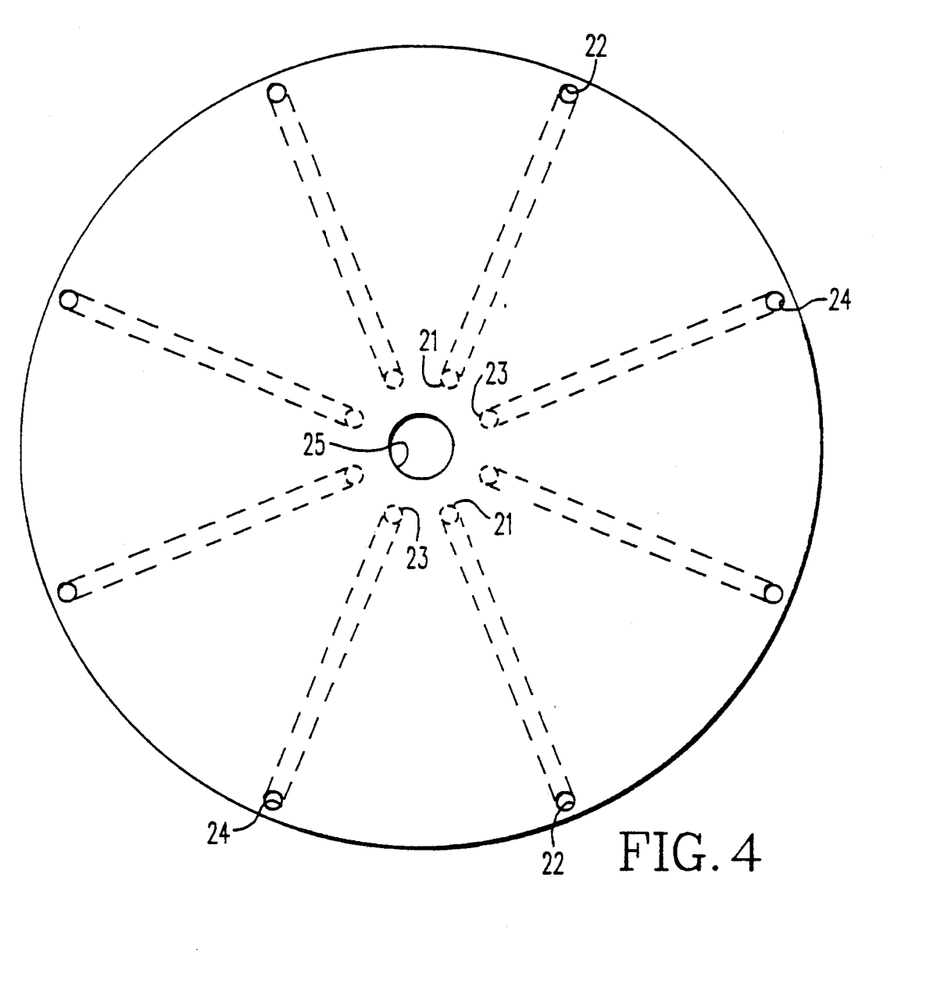
FIG. 4 is a plan view of the bottom of the item shown in FIG. 3.
Figure 5:
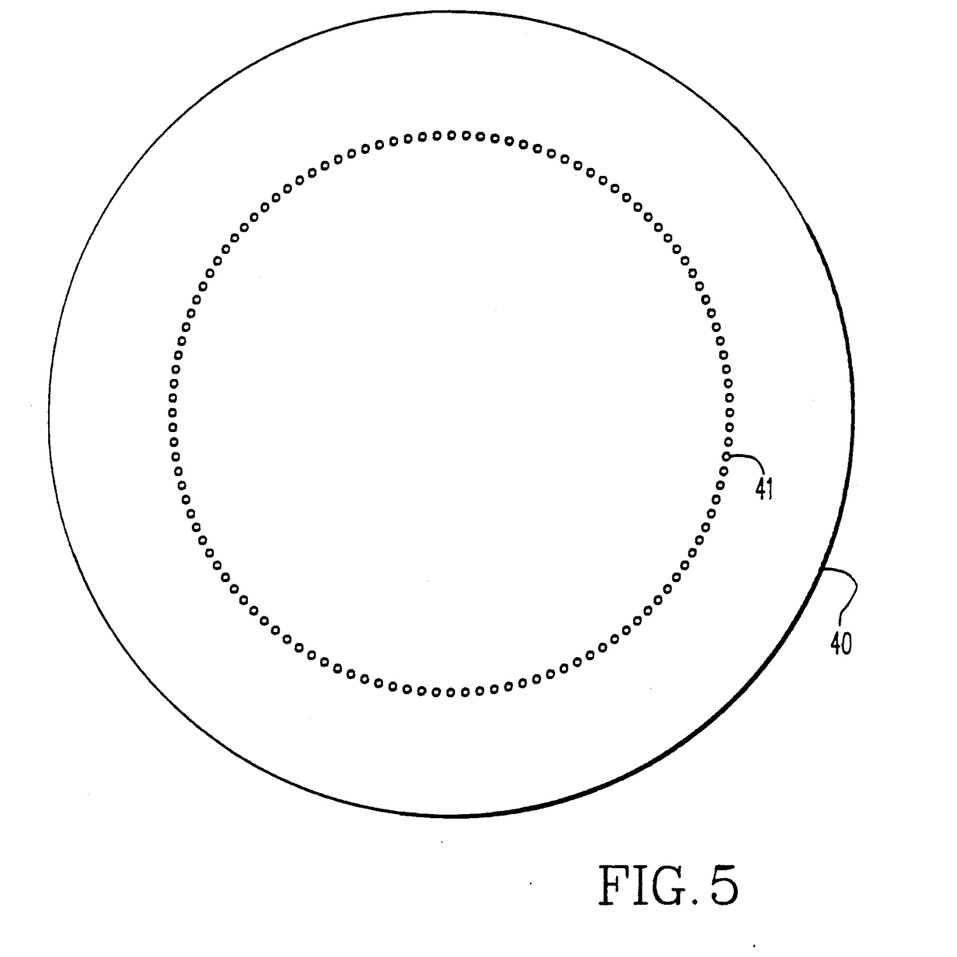
FIG. 5 is a plan view of the bottom of the CAC.

The bottom of the annular space 32 is defined by a product plate 40. As seen in FIG. 5, a large number of product delivery channels or pipes 41 pass through this plate. This allows the collection of a variety of product fractions and also facilitates adjustments to the operating conditions to allow product collection at various angular displacements.

The distributor plate 20 is held in a fixed position above the annular space 32 by a bracket 62 which is turn connected to a support rod 61 which is affixed to a base plate 60. Also affixed to this base plate 60 is a support column 63 on which the product plate 40 rotatably rests. A shaft 70 passes through this support column 63 and base plate 60 and connects the product plate 40 to a motivating means not shown. Also affixed to the base plate 60 is an annular collection trough 50 which can be subdivided into any number of convenient segments, each with its own exit port 51.

The continuous annular chromatograph 10 is operated by rotating the annular space 32 packed with the resin beads 27 beneath the fixed distributor plate 20 and its associated feed nozzles 22 and 24. The rotational force is supplied by the shaft 70.

We claim:

1. A continuous chromatographic process for the simultaneous separation of each of the isotopes of zirconium in a sample containing a mixture of zirconium isotopes to produce substantially pure fractions of each of said separated isotopes, wherein said process includes the steps of:
   (a) loading a substantially vertical chromatographic separation column having an effective column height sufficient to resolve each said zirconium isotope into a distinct product fraction having a purity greater than 90% with a cation exchange resin including pentavalent phosphorus-derived active groups having a strong affinity for zirconium cations and complexes thereof;
   (b) preparing an aqueous feed solution of ionic zirconium from said sample having a pH of between about 3 and 4 and a solubility limit of about 90 g/l;
   (c) preparing an eluant capable of displacing zirconium ions from said exchange resin, wherein said eluant is an aqueous solution of a strong mineral acid having a normality greater than one;
   (d) feeding said aqueous zirconium feed solution to the top of said located chromatographic separation column so that said feed solution begins to travel down said column;
   (e) feeding said mineral acid eluant through said column to cause each of the zirconium isotopes in said feed solution to pass through said column at a different speed;
   (f) collecting a separate zirconium isotope containing product fraction at the bottom of said column for each of the isotopes present in said sample; and
   (g) containing to feed said eluant through said column until each of said zirconium isotopes present in said sample has been separated and collected.

2. The process described in claim 1, wherein said cation exchange resin includes pentavalent phosphorus-derived active groups selected from the group consisting of tributyl phosphate, tri-n-octyl phosphine oxide, di-2-ethylhexyl phosphoric acid and mixtures thereof.

3. The process described in claim 2, wherein said active groups comprise di-2-ethylhexyl phosphoric acid.

4. The process described in claim 3, wherein said cation exchange resin comprises resin beads having an average particle size of less than 10 microns and said resin beads include said di-2-ethylhexyl phosphoric acid active groups.

5. The process described in claim 1, wherein the cation exchange resin including said pentavalent phosphorus-derived active groups is a monodisperse distribution of spherical beads having an average particle size of about one micron or less and an exchange capacity of between 0.01 and 0.5 milliequivalents for zirconium cations.

6. The process described in claim 1, wherein the separation factor of said column for a theoretical stage having a height of 25 cm for zirconium-90 is at least about 1.05.

7. The process described in claim 1, wherein said zirconium isotope-containing sample additionally contains hafnium and said hafnium is separated from said zirconium isotopes during said continuous chromatographic process and collected as a separate fraction in steps (f) and (g).

8. The process described in claim 1, wherein said chromatographic separation column is located in the circumferential annular space of a continuous annular chromatograph.

9. The continuous steady state chromatographic process for simultaneously producing commercially useful quantities of zirconium isotopes with low thermal neutron capture cross-sections including the steps of:
   (a) preparing an acidic aqueous feed solution of a zirconium compound containing said zirconium isotopes;
   (b) preparing a stationary phase comprising a cation exchange resin with a monodisperse particle distribution of substantially spherical particles having an average particle size less than or equal to about 1 micron, said particles including active groups comprising pentavalent phosphorus-derived compounds having a strong affinity for zirconium cations and a capacity for zirconium cations of between about 0.01 and 0.5 meq/ml, and a separation factor for zirconium-90 for a 25 cm theoretical stage of at least about 1.05;

(c) loading said stationary phase including said pentavalent phosphorus-derived active groups into the circumferential annular space of a continuous annular chromatograph so that the effective height of the stationary phase is sufficient to yield a zirconium-90 product fraction comprising 98 mol percent zirconium-90;

(d) while said chromatograph is rotating feeding said zirconium isotope-containing feed solution to the continuous annular chromatograph so that said feed solution penetrates about 1% of the effective height of the stationary phase;

(e) feeding a continuous supply of an acid eluant having a normality between about 3 and 6 into the top of the annular stationary phase to at least one circumferential location;

(f) while the continuous annular chromatograph is rotating, continuing to feed said zirconium isotope-containing feed solution and said eluant into the annular pentavalent phosphorus-derived active group-containing stationary phase;

(g) after all of the zirconium isotopes present in said feed solution have been eluted, collecting a separate product fraction corresponding to each said low thermal neutron cross-section zirconium isotope present in said aqueous feed;

(h) continuously repeating steps (d) through (g) to produce said commercially useful quantities of said low thermal neutron cross-section zirconium isotopes.

10. The process described in claim 1, wherein said pentavalent phosphorus-derived compounds are selected from the group consisting of tributyl phosphate, tri-n-octyl phosphine oxide, di-2-ethylhexyl phosphoric acid and mixtures thereof.

11. The process described in claim 1, wherein said pentavalent phosphorus-derived compound is di-2-ethylhexyl phosphoric acid.

12. The process described in claim 1, wherein said zirconium isotope-containing compound is zirconium oxychloride and said eluant is hydrochloric acid.

13. The process described in claim 1, wherein said eluant is fed into the annular stationary phase at a plurality of circumferential locations and the concentration of said acid eluant is increased at each successive feed location moving in the direction of rotation of the continuous annular chromatograph.

14. The process described in claim 9, wherein said zirconium isotope-containing compound further contains hafnium and said process separates said hafnium from each said zirconium isotope to produce separate product fractions comprising hafnium and each zirconium isotope contained in said compound.

15. The process described in claim 10, wherein said zirconium isotope product fractions comprise zirconium-90 and zirconium-94.

* * * * *